(12) United States Patent
Grab et al.

(10) Patent No.: US 7,585,535 B2
(45) Date of Patent: Sep. 8, 2009

(54) FLAVOUR AND FRAGRANCE COMPOSITIONS

(75) Inventors: Willi Grab, Singapore (SG); Stephan Furrer, Cincinnati, OH (US); Damian John Ratcliff, Singapore (SG)

(73) Assignee: Givaudan SA, Vernier (CH)

( * ) Notice: Subject to any disclaimer, the term of this patent is extended or adjusted under 35 U.S.C. 154(b) by 744 days.

(21) Appl. No.: 10/479,453

(22) PCT Filed: Jun. 3, 2002

(86) PCT No.: PCT/CH02/00288

§ 371 (c)(1),
(2), (4) Date: Jul. 29, 2004

(87) PCT Pub. No.: WO02/098241

PCT Pub. Date: Dec. 12, 2002

(65) Prior Publication Data

US 2004/0253362 A1 Dec. 16, 2004

(30) Foreign Application Priority Data

Jun. 6, 2001 (EP) .................................. 01113787

(51) Int. Cl.
*A23L 1/22* (2006.01)
(52) U.S. Cl. ...................................... 426/535; 426/534
(58) Field of Classification Search ................ 426/534, 426/535, 536, 538, 650
See application file for complete search history.

(56) References Cited

U.S. PATENT DOCUMENTS 3,968,264 A 7/1976 Winter et al. ............... 426/535
4,277,024 A 7/1981 Spector ....................... 239/36

FOREIGN PATENT DOCUMENTS

| GB | 1438790 | 6/1979 |
|---|---|---|
| GB | 2 055 689 A | 3/1981 |
| GB | 2 235 869 A | 3/1991 |
| GB | 2 347 644 A | 9/2000 |

OTHER PUBLICATIONS

Asakura et al, Antioxidant Effect and Antimicrobial Activity of Phenolic Sulfides, JAOCS, vol. 66, No. 10 (Oct. 1989), pp. 1450-1453.*
GB 0114572.1 Search Report dated Jan. 3, 2002.
PCT International Search Report, dated Aug. 15, 2002 for PCT/CH02/00288.

* cited by examiner

*Primary Examiner*—Leslie Wong
(74) *Attorney, Agent, or Firm*—Norris, McLaughlin & Marcus, PA

(57) ABSTRACT

Flavor and fragrance compositions comprising 1-mercapto-1-arylalkanes or derivatives thereof according to formula (I)

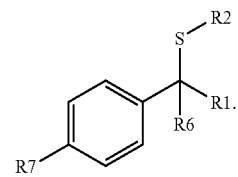

16 Claims, No Drawings

FLAVOUR AND FRAGRANCE COMPOSITIONS

This application is a 371 of PCT/CH02/00288 filed Jun. 3, 2002.

This invention is concerned with flavour and fragrance compositions containing 1-mercapto-1-arylalkanes, in particular 1-mercapto-1-phenylalkanes and to methods of flavouring or adding fragrance or aroma to a food, beverage or a consumer healthcare or household product using these compounds.

The flavour and fragrance industry is continuously interested in new ingredients that may impart to a product a clear, natural spicy, roasted and fruity character.

Both benzylmercaptan and 2-phenylethylmercaptan have found use in the flavours industry for the strong roasted note that they impart to meat and coffee flavours. However, the use of these compounds in the flavours industry is limited, and of practically no use in the fragrance industry, because of their characteristic dominant roasted note which is also accompanied by pungent and slightly putrid notes.

It might be expected that molecules possessing a similar structure to benzylmercaptan and 2-phenylethylmercaptan would express similar characteristic notes. In fact, just such a structurally similar molecule—1-mercapto-1-phenylethane—has been found in volatiles of the defence secretion of skunks and in the volatiles of fermented household waste.

Surprisingly, however, we have now found that certain 1-mercapto-1-arylalkanes and derivatives thereof impart to products the clear, natural spicy, roasted and fruity character so desired by the flavour and fragrance industry, without any attendant dominant roasted note or accompanying pungent and putrid notes.

Accordingly, the invention provides in one of its aspects a flavour or fragrance composition comprising a compound of formula (I)

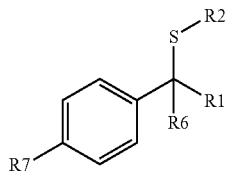

wherein R1 represents an alkyl group having from 1 to 4 carbon atoms which may be branched or unbranched; R2 represents, hydrogen; a lower alkyl group, e.g. methyl, ethyl, or branched or linear propyl or butyl; acyl, in particular selected from the group —(R3)C=O wherein R3 represents a branched or unbranched alkyl group having from 1 to 4 carbon atoms; or an alkoxyalkyl group, in particular selected from the group —CH(R4)—OR5, wherein R4 represents hydrogen or a branched or unbranched alkyl group having from 1 to 4 carbon atoms; R5 represents a branched or unbranched alkyl group having from 1 to 4 carbon atoms; R6 represents hydrogen or methyl; and R7 represents hydrogen, methyl or alkoxy having 1 to 4 carbon atoms, e.g. methoxy.

R1, R3, R4 and R5 independently are particularly represented by methyl, ethyl, n-, or iso-propyl, and n-, or iso-butyl. R2 is particularly represented by hydrogen, formyl, acetyl, propionyl, butyryl, isobutyryl, 1'-ethoxyethyl, 1-methoxyethyl, or 2'(2'-methoxypropyl).

Particularly preferred compounds for use in compositions according to the invention are selected from 1-mercapto-1-phenylethane, 1-mercapto-1-phenylpropane, 1-mercapto-1-phenylbutane, 1-mercapto-1-phenylisobutane, 1-mercapto-1-(p-methylphenyl)-ethane, 1-mercapto-1-(p-methylphenyl)-propane, and 2-mercapto-2-(p-methylphenyl)-propane. Most preferred are 1-mercapto-1-phenylethane, 1-mercapto-1-phenylpropane and 2-mercapto-2-(p-methylphenyl)-propane.

A compound of formula (I) may be used in its enantiomerically pure form, however, as the R and S enantiomers were found to have essentially similar activity as flavour or fragrance materials, it is preferred to use the more easily accessible and therefore cheaper racemate.

The invention provides in another of its aspects a compound of formula (I) selected from those disclosed in the Examples as Examples 3, 9, 10, 11, 12, 13, 14, 15 and 17.

The mercapto-compounds of formula (I) (i.e. R2=H) may be synthesised from commonly available starting materials and reagents according to synthetic protocols known in the art. Acylmercapto-compounds (i.e. R2=acyl), e.g. acetylmercapto-compounds of the formula (I) may be synthesised from the corresponding alcohol, e.g. 1-phenyl-1-propanol, and thioacetic acid in the presence of zinc chloride according to standard synthetic protocols known in the art. Alkoxyalkylmercapto compounds of formula (I) (i.e. R2=alkoxyalkyl) may be formed, for example by reacting the corresponding mercapto-compound with, for example ethyl-vinyl-ether under acid catalysis according to standard synthetic protocols. Similarly, the sulphides (R2=alkyl) may be simply prepared from the mercapto-compounds by alkylating at the sulphur atom according to standard synthetic protocols.

The resolution of the compounds of the formula (I) into their enantiomeric forms may also be effected in a manner known in the art.

Compositions according to the present invention may contain one or more compounds of the formula (I). Alternatively, the compositions may contain one or more precursors of compounds of the formula (I). By "precursors" is meant certain derivatives that may be transformed into a compound of formula (I), for example over an extended period of time during storage, and/or as a result of the application of an exogenous physical stimulus, for example the application of heat and/or light to the product containing said precursors, or by some chemical stimulus such as hydrolysis, e.g. enzymatic hydrolysis. As a further alternative, a composition according to the invention may contain one or more compounds of formula (I) and one or more precursors. Precursors independently may have properties as flavourants or odourants.

As precursors come into consideration, in particular, thioesters of compounds of formula (I), in particular thioesters of lower fatty acids, e.g. $C_1$ to $C_6$ fatty acids, and carbonates of compounds of the formula (I). These precursors may be obtained by reacting a compound of formula (I) with an acyl chloride. Other precursors include thioacetals of lower aldehydes, for example acetaldehyde and propionaldehyde, which may be obtained by reacting the corresponding mercapto-compound with, for example an alkyl-vinyl-ether. Still further, the sulphides (R2=alkyl) may be considered as precursors as they can easily be reduced to thiols (R2=H).

It is to be understood that certain compounds of formula (I), whereas they are useful as flavourants and odourants in their own right, may act as precursors for certain other compounds of formula (I), for example, those compounds wherein R=acyl or alkoxyalkyl may act as precursors for compounds wherein R=H.

The flavourant and odourant qualities of compounds of the formula (I) and precursors thereof may be evident over a broad range of concentrations. For example, in the case of a food, a beverage, a consumer healthcare product or a household product a compound or precursor may be present in amounts ranging from 0.0001 to 500 mg/Kg, more preferably 0.01 to 50 mg/Kg. Whereas, in the case of a fragrance composition a compound or a precursor may be present in a concentration ranging from 0.00001% to 1%, more preferably 0.001% to 0.1%.

The compounds of formula (I) and/or precursor compounds may be mixed with any ingredients useful in flavour or fragrance compositions. In particular, they may be combined with one or more of the extensive range of natural, synthetic, nature identical, natural odourant or flavourant materials or natural extracts used in the flavour or fragrance fields.

Additionally, compositions may contain one or more ingredients or excipients commonly used in conjunction with flavourants and odourants, for example carrier materials, thickeners, flavour enhancers and other auxiliary agents commonly known and used in the art.

Compositions according to the invention may be employed in all the customary fields of application. Particular embodiments of the invention include compositions for use in fragrance applications, for example fine fragrance applications or perfumed products of all kinds, for example luxury perfumes, cosmetic articles, consumer healthcare products or household products, e.g. washing agents, detergents, soaps and toothpaste. Other particular embodiments include the use in flavour applications, for example in foodstuffs, beverages, pharmaceuticals, oral hygiene products and other healthcare products wherein it is customary to use flavourants.

The compounds of formula (I) and/or their precursor compounds add fruity, spicy and some tropical aspects to fruit flavour and vegetable compositions such as citrus, chilli and papaya. The top note of the flavour of such products is increased and modified in a natural direction. However, the use of compounds of formula (I) is not limited to fruit flavours. Thus, compounds of the present invention may be combined with savoury, herbal and mint flavours to enhance natural herbal and spicy flavours. In a particular embodiment, compounds of formula (I) may be used to enhance the natural spicy aroma and flavour of Asian curry flavours.

There now follows a series of examples that serve to illustrate the invention.

SYNTHESIS EXAMPLES

Thioacetic acid S-(1-phenyl-ethyl)ester:
In a synthesis carried our according to Gauthier, Bourdon, Young, Tetrahedron Lett., 27(1), 15 (1986), at room temperature, 16.3 g of zinc iodide, 100 mL of dichloromethane and 12.5 g of 1-Phenyl-1-ethylalcohol are added to a 250 ml round-bottom flask. To this suspension 9.52 g of thioacetic acid is added. The mixture is stirred for 16 hours at room temperature. The reaction mixture is extracted with dichloromethane. The organic layer is washed with brine, dried over magnesium sulphate, filtered and concentrated to give 18.2 g of a yellow liquid which is purified by chromatography on silica gel.

1-Mercapto-1-phenylethane:
In a synthesis carried out according to Hoppe, et al., Angew. Chem. Int. Ed., 36(24), 2784 (1997), at room temperature, 2.1 g of lithium aluminum hydride and 100 mL of methyl tertiary butyl ether are added to a 250 mL round-bottom flask. To this suspension 18 g of thioacetic acid S-(1-phenyl-ethyl)ester in 50 mL MTBE is added. The mixture is stirred for 15 h at room temperature. 5 mL of ethyl acetate and 2.5 mL of sodium hydroxide (1 M in water) are added. The reaction mixture is filtered over a sodium sulphate plug. The filtrate is concentrated to give 13.7 g of a yellow liquid which is purified by distillation.

(S)-1-Mercapto-1-phenylethane:
In a synthesis carried out according to EP-0480716, Merck Frosst Canada Inc., (1992), and Hoppe, et al., Angew. Chem. Int. Ed., 36(24), 2784 (1997), at −10° C., 2.6 g of triphenyl phosphine and 35 mL tetrahydrofuran are added to a 100 mL round-bottom flask. To this solution 1.74 g of diethyl azo dicarboxylate are added. The solution is stirred for 8 hours at −10° C., at which time it became a beige suspension. A solution of 0.61 g of (R)-1-Phenyl-1-ethanol, 0.78 g of thioacetic acid in 7.5 mL tetrahydrofuran is added at −10° C. The mixture is stirred for 16 hours at room temperature. The reaction mixture is concentrated, suspended in hexane and filtered. The filtrate is washed with brine, dried over magnesium sulfate, filtered, concentrated and purified by column chromatography on silica gel to give 0.58 g yellow liquid. This is reacted as described in the synthesis of 1-mercapto-1-phenylethane as described above to give 0.35 g of (S)-1-mercapto-1-phenylethane.

Thiobutyric acid S-(1-phenyl-ethyl)ester:
At room temperature, 13.8 g of 1-mercapto-1-phenylethane is dissolved in 50 mL of butyryl chloride. The mixture is stirred at room temperature for 6 hours. It is then cooled down to 0° C. and the reaction is quenched by careful addition of 100 ml of dry methanol in small portions. The mixture is then washed with bicarbonate, dried over magnesium sulfate, filtered and concentrated to give the butyrated compound in 98% yield.

1-(Methylthio)-1-phenylethane:
At 0° C., 2.24 g sodium thiomethoxide and 25 mL tetrahydrofuran are added to a 100 mL flask. 5.89 g (1-bromoethyl) benzene in 5 mL tetrahydrofurane are added and the mixture is stirred for 16 hours at room temperature. The reaction mixture is extracted with MTBE/brine. The organic layer is washed with brine, dried over magnesium sulfate and concentrated to give the methylthio compound in 90% yield.

Table 1 discloses compounds of the general formula set forth below, that may be formed according to an appropriate method analogous to those described above, employing corresponding starting materials. In all cases, the compounds are formulated into fragrance compositions to provide sparkling and diffusive accords, and into foods and beverages to impart strong fruity or spicy aspects.

TABLE 1

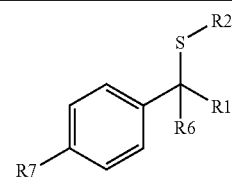

| Example | R1 | R2[a] | R6 | R7 |
|---|---|---|---|---|
| 1 | Methyl | H | H | H |
| 2 | Ethyl | H | H | H |
| 3 | n-butyl | H | H | H |
| 4 | Methyl | H | H | methyl |
| 5 | Methyl | H | H | methoxy |
| 6 | Methyl | H | methyl | H |
| 7 | Methyl | methyl | H | H |
| 8 | Methyl | A | H | H |

TABLE 1-continued

| Example | R1 | R2(a) | R6 | R7 |
|---|---|---|---|---|
| 9 | Ethyl | A | H | H |
| 10 | n-butyl | A | H | H |
| 11 | Methyl | A | H | methyl |
| 12 | Methyl | A | H | methoxy |
| 13 | Methyl | B | H | H |
| 14 | Methyl | C | H | H |
| 15 | Methyl | D | H | H |
| 16 | Methyl | A | methyl | H |
| 17 | Methyl | E | H | H |

(a) = The residues A through E are represented by the formula:-

$$\underset{Y}{\overset{O}{\|}}$$

wherein in residue A, Y=methyl; in residue B, Y=ethyl; in residue C, Y=propyl; in residue D, Y=iso-propyl; and in residue E, Y=hydrogen.

TABLE 2

Characterising data for selected compounds

Example

1
1H-NMR 7.4-7.2(m, 5H), 4.2(quintet, 1H), 2.0(d, 1H), 1.7(d, 3H)
MS 138(M+), 121, 105, 91, 77

2
1H-NMR 7.3-7.2(m, 5H), 3.9(quintet, 1H), 2.0-1.9(m, 3H), 0.9(t, 3H)
MS 152(M+), 123, 119, 103, 91, 77

3
1H-NMR 7.3-7.2(m, 5H), 4.0(quartet, 1H), 2.0-1.9(m, 3H), 1.4-1.3(m, 4H), 0.9(t, 3H)
MS 180(M+), 147, 123, 105, 91, 77

4
1H-NMR 7.3(d, 2H), 7.1(d, 2H), 4.2(quintet, 1H), 2.3(s, 3H), 2.0(d, 1H), 1.7(d, 3H)
MS 152(M+), 135, 119, 103, 91, 77

5
1H-NMR 7.3(d, 2H), 6.8(d, 2H), 4.3(quintet, 1H), 3.8(s, 3H), 2.0(d, 1H), 1.7(d, 3H)
MS 168(M+), 151, 135, 120, 105, 91, 77

6
1H-NMR 7.6(d, 2H), 7.3(t, 2H), 7.2(t, 1H), 2.3(s, 1H), 1.9(siglet, 6H)
MS 152(M+), 137, 119, 103, 91, 77

7
1H-NMR 7.3-7.2(m, 5H), 3.9(quartet, 1H), 1.9(s, 3H), 1.6(d, 3H)
MS 152(M+), 137, 121, 105, 91, 77

8
1H-NMR 7.4-7.2(m, 5H), 4.8(quartet, 1H), 2.3(s, 3H), 1.7(d, 3H)
MS 180(M+), 138, 121, 105, 91, 77

TABLE 2-continued

Characterising data for selected compounds

Example

9
1H-NMR 7.3-7.2(m, 5H), 4.5(t, 1H), 2.3(s, 3H), 2.0(quintet, 2H), 0.9(t, 3H)
MS 194(M+), 165, 152, 135, 119, 103, 91, 77

11
1H-NMR 7.3(d, 2H), 7.1(d, 2H), 4.7(quartet, 1H), 2.3(s, 3H), 2.3(s, 3H), 1.6(d, 3H)
MS 194(M+), 151, 135, 119, 103, 91, 77

12
1H-NMR 7.1(d, 2H), 6.7(d, 2H), 4.6(quartet, 1H), 3.6(s, 3H), 2.1(s, 3H), 1.5(d, 3H)
MS 210(M+), 167, 151, 135, 120, 105, 91, 77

13
1H-NMR 7.3-7.2(m, 5H), 4.7(quartet, 1H), 2.5(quartet, 2H), 1.7(d, 3H), 1.2(t, 3H)
MS 194(M+), 165, 138, 121, 105, 91, 77

14
1H-NMR 7.3-7.2(m, 5H), 4.8(quartet, 1H), 2.5(t, 2H), 1.7(m, 5H), 1.0(t, 3H)
MS 208(M+), 175, 165, 138, 121, 105, 91, 77

15
1H-NMR 7.3-7.2(m, 5H), 4.7(quartet, 1H), 2.7(septlet, 1H), 1.7(d, 3H), 1.2(t, 6H)
MS 208(M+), 165, 138, 121, 105, 91, 77

16
1H-NMR 7.6(d, 2H), 7.3(t, 2H), 7.2(t, 1H), 2.2(s, 3H), 1.9(s, 6H)
MS 194(M+), 151, 137, 119, 103, 91, 77

17
1H-NMR 10.1(s, 1H), 7.4-7.3(m, 5H), 5.0(quartet, 1H), 1.7(d, 3H)
MS 166(M+), 135, 121, 105, 91, 77

Formulation Example 1

0.08 mg/l 1-mercapto-1-phenyl-ethane was added to a tropical fruit soft drink of composition (a) containing the fruit flavour (b). Comparing the resultant composition with the aroma note of the starting soft drink, an additional typical top note was detected and, at the same time, the persistence was increased significantly.

| | [g] |
|---|---|
| (a): Composition of typical tropical fruit soft drink: | |
| water: | 9400 |
| orange juice concentrate | 100 |
| sugar syrup 65 Brix: | 170 |
| citric acid 50%: | 5 |
| sodium citrate: | 0.4 |
| sodium benzoate: | 0.15 |
| tropical fruit flavour (b): | 10 |
| (b): Composition of tropical fruit flavour | |
| Lemon oil green | 100 |
| Tangerine oil cold pressed | 300 |
| Orange oil 7.8 fold | 200 |
| Sinensal fraction ex orange oil | 5 |
| Ethyl butyrate | 10 |
| Allylhexanoate | 5 |
| Acetaldehyde | 30 |

-continued

| | [g] |
|---|---|
| Orange oil Brazil | 340 |
| Key component (1% in Triacetin) | 10 |

Formulation Example 2

The effect of 1-mercapto-1-phenyl-ethane, and the structurally similar molecules benzylmercaptan and 2-phenylethylmercaptan on an orange soft drink (blank) was examined.

The aforementioned compounds were added at a level of 0.1 mg/L and compared with the blank orange soft drink. The drink containing 1-mercapto-1-phenyl-ethane exhibited an orange, mandarin, fresh squeezed juice note with strong fruity aspects, typical of oranges found in Asia, which is a significant improvement over the blank soft drink. In contrast thereto, the drinks containing benzylmercaptan or 2-phenylethylmercaptan had a strong roasted, even slightly putrid note, which did not blend well with the fruity aspect.

| Composition of orange soft drink: | |
|---|---|
| | [g] |
| water: | 9500 |
| sugar syrup 65 Brix: | 170 |
| citric acid 50%: | 5 |
| sodium citrate: | 0.4 |
| sodium benzoate: | 0.15 |
| orange oil 40 fold: | 0.005 |

Formulation Example 3

| Curry sauce | |
|---|---|
| Sugar | 120.0 |
| Xanthan Gum | 0.40 |
| Salt | 60.0 |
| Citric Acid | 0.80 |
| Modified Starch Coflo 67 | 24.0 |
| Ground Onion Powder | 48.0 |
| Ground Garlic Powder | 10.0 |
| Ground Curry Powder | 20.0 |
| Soyarome | 5.6 |
| Tomato Paste | 33.6 |
| Vegetable Oil | 104.0 |
| Water | 560.0 |
| Chicken Flavour | 2.4 |
| Gourmax Coconut Milk | 8.0 |
| Curry Flavour | 3.2 |
| Total | 1000.0 |

Preparation Method (Laboratory Scale)
1) Xanthan gum and sugar were premixed and left to one side.
2) The remaining ingredients, except flavours, were added to a pot and cooked at medium heat until the sauce started to thicken. The premix of gum and sugar were added and cooking continued until the temperature reached 85 degrees centigrade. Thereafter, the sauce was left to stand for at least 5 minutes. Afterwards, the flavours were added and stirred well to dissolve. The sauce was then filled into glass bottles and sterilised. Optionally a preservative such as sodium benzoate is added to prolong the shelf life.

| Curry Flavour | |
|---|---|
| Anise Oil | 0.6 |
| Clove Oleoresin | 0.3 |
| Coriander Oleoresin | 24.0 |
| Cumin Oleoresin | 8.0 |
| Cinnamon Oleoresin | 0.6 |
| Ginger Oleoresin | 2.0 |
| Black Pepper Oleoresin | 3.0 |
| Oleoresin Turmeric | 8.0 |
| Palm Olein | q.s. |
| Capsicum Oleoresin | 30.0 |
| Total | 1000.0 |

The addition of 0.01% of a 1% solution of 1-mercapto-1-phenyl-ethane added a very natural spicy note to the curry sauce, which was well appreciated by Indian and Asian people. The addition of 0.01% of a 1% of benzylmercaptan or 2-phenylethylmercaptan conversely, added a burnt, roasted note to the curry sauce.

Formulation Example 4

Comparison of Fragrance Accords:

Either 0.004% (w/w) of 1-mercapto-1-phenyl-ethane, benzylmercaptan or 2-phenylethylmercaptan were added to a clementine accord as described below. At a very low level the accord turned from orange to a natural mandarin with 1-mercapto-1-phenyl-ethane. The sample was more sparkling, natural clementine and strongly diffusive. When benzylmercaptan or 2-phenylethylmercaptan were used instead, the samples were less diffusive and a disturbing sulphurous, burnt, putrid side note appeared.

| Formula of clementine accord | |
|---|---|
| rose oxide | 1 |
| buchu leaf oil | 2 |
| geranyl acetate | 3 |
| geranyl butyrate | 3 |
| ethyl caprylate | 4 |
| (E)-2-hexenal | 4 |
| geranyl isobutyrate | 4 |
| cinnamic aldehyde | 5 |
| oxane 5% in dipropylene glycol | 5 |
| hexanal | 6 |
| (Z)-3-hexenol | 6 |
| linalool oxide | 6 |
| isoeugenol acetate | 7 |
| corps pampelmousse 10% in triethyl citrate | 10 |
| benzaldehyde | 15 |
| allyl heptanoate | 15 |
| cinnamyl acetate | 20 |
| beta ionone | 24 |
| ethyl acetoacetate | 60 |
| gamma undecalactone | 80 |
| ethyl acetate | 120 |
| labienoxime | 200 |
| lemon oil Italy | 600 |
| furonol 1% in triethyl citrate | 1060 |
| orange oil 7-fold | 2000 |
| orange oil brasil | 2400 |
| dipropylene glycol | 3340 |
| | 10000 |

The invention claimed is:

1. A flavour or fragrance composition comprising a compound of the formula (I)

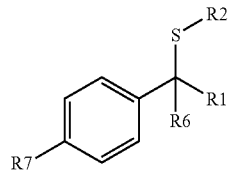

wherein:
R1 is an alkyl group having from 1 to 4 carbon atoms which may be branched or unbranched;
R2 is selected from hydrogen; a lower alkyl group, in particular methyl, ethyl, or linear or branched propyl or butyl; an acyl group, in particular —(R3)C═O wherein R3 represents a branched or unbranched alkyl group having from 1 to 4 carbon atoms; or is an alkoxyalkyl group, in particular —CH(R4)—OR5, wherein R4 is selected from hydrogen or is a branched or unbranched alkyl group having from 1 to 4 carbon atoms; and R5 is selected from a branched or unbranched alkyl group having from 1 to 4 carbon atoms;
R6 is selected from hydrogen or methyl; and
R7 is selected from hydrogen, methyl or alkoxy groups having 1 to 4 carbon atoms.

2. A composition according to claim 1 wherein R1 is an alkyl group selected from methyl, ethyl, n-propyl, iso-propyl, n-butyl, and iso-butyl.

3. A composition according to claim 1 wherein R2 is selected from hydrogen, acetyl or 1'-ethoxyethyl.

4. A composition according to claim 1 wherein the compound of formula (I) is selected from 1-mercapto-1-phenylethane, 1-mercapto-1-phenylpropane, 1-mercapto-1-phenylbutane, 1-mercapto-1-phenylisobutane, 1-mercapto-1-(p-methylphenyl)-ethane, 1-mercapto-1-(p-methylphenyl)-propane, and 2-mercapto-2-(p-methylphenyl)-propane.

5. A flavour or fragrance composition comprising 1-mercapto-1-phenylethane according to claim 1 in the form of its thioester, thioacetal, thioacetate, thioformate or thioacetaldehyde-ethylacetal.

6. A flavoured product comprising a compound of formula (I) according to claim 1 present in the flavoured product in an amount ranging from 0.0001 to 500 mg/kg.

7. A flavoured product according to claim 6 selected from the group which includes: a food, a beverage, a pharmaceutical, an oral hygiene product or a healthcare product.

8. A fragranced product comprising a compound of formula (I) according to claim 1 present in the fragranced product in an amount ranging from 0.00001% to 1%.

9. A fragranced product according to claim 8 wherein the fragranced product is a fine fragrance product.

10. A composition comprising a precursor of a compound according to formula (I) according to claim 1 in addition to a compound according to formula (I).

11. A method of improving a flavour or fragrance composition comprising the step of adding thereto a compound of formula (I) according to claim 1 or a precursor thereof to the flavour or fragrance composition.

12. A compound according to formula (I) according to claim 1

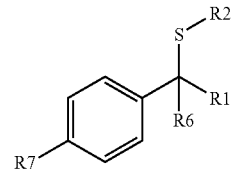

wherein,
R2, R6 and R7 are hydrogen and R1 is n-butyl.

13. A compound according to formula (I) according to claim 1

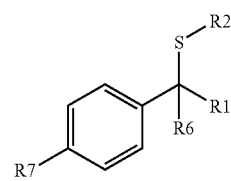

wherein,
R2 is acetyl, R6 and R7 are hydrogen, and R1 is ethyl or n-butyl.

14. A compound according to formula (I) according to claim 1

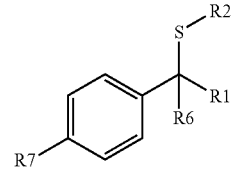

wherein,
R2 is acetyl, R1 is methyl, R6 is hydrogen, and R7 is methyl or methoxy.

15. A compound according to formula (I) according to claim 1

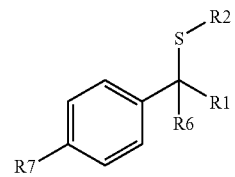

wherein,
R2 is $C_2H_5C$═O, $nC_3H_7C$═O or $i\text{-}C_3H_7C$═O, R1 is methyl, and R6 and R7 are hydrogen.

16. A compound according to formula (I) according to claim 1

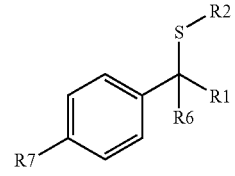

wherein,
R2 is HC═O, R1 is methyl, and R6 and R7 are hydrogen.

* * * * *

UNITED STATES PATENT AND TRADEMARK OFFICE
CERTIFICATE OF CORRECTION

PATENT NO. : 7,585,535 B2  Page 1 of 1
APPLICATION NO. : 10/479453
DATED : September 8, 2009
INVENTOR(S) : Grab et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1412 days.

Signed and Sealed this

Fourteenth Day of September, 2010

David J. Kappos
*Director of the United States Patent and Trademark Office*